US 6,558,499 B1

(12) United States Patent
Pargass et al.

(10) Patent No.: US 6,558,499 B1
(45) Date of Patent: May 6, 2003

(54) DISPOSABLE ABSORBENT ARTICLE HAVING GRAPHICS AND PROCESS FOR MAKING

(75) Inventors: Sunita Pargass, Norcross, GA (US); Joseph B. Vergona, Suwanee, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/543,781

(22) Filed: Apr. 6, 2000

Related U.S. Application Data
(60) Provisional application No. 60/177,227, filed on Jan. 21, 2000.

(51) Int. Cl.[7] .......................... B32B 31/18; B32B 3/06; G05G 15/00; B26D 5/00; A61F 13/15

(52) U.S. Cl. .................. 156/250; 156/264; 156/350; 156/354; 428/74; 428/79; 428/95; 428/195; 116/200; 604/361; 604/385.03; 604/389

(58) Field of Search .................. 156/435, 178, 156/264, 302, 354, 529, 250, 251, 248, 256, 257, 263, 277, 384, 510, 555, 517, 350; 604/361, 385.63, 391, 387, 389, 390; 428/74, 78, 79, 95, 99, 195, 206; 116/200, 206, 207, 208, 211, 216

(56) References Cited

U.S. PATENT DOCUMENTS 5,235,515 A * 8/1993 Ungpiyakul et al. ........ 364/469

* cited by examiner

Primary Examiner—J. A. Lorengo
(74) Attorney, Agent, or Firm—Hunton & Williams

(57) ABSTRACT

An absorbent article including one or more graphics thereon and a method for making the same are provided according to the present invention, wherein the reference markers used to cut the graphics are not included on the final absorbent article. Further, a variety pack of absorbent articles and method for making the same are provided, wherein each absorbent article in the pack includes a graphic thereon which differs from the graphics on the other absorbent articles in the pack.

6 Claims, 9 Drawing Sheets

DISPOSABLE ABSORBENT ARTICLE HAVING GRAPHICS AND PROCESS FOR MAKING

This application claims the benefit of Provisional Application No. 60/177,227 filed Jun. 21, 2000.

FIELD OF THE INVENTION

The present invention relates to disposable absorbent articles, and more particularly to disposable absorbent articles having graphics thereon, and processes for making the same.

BACKGROUND OF THE INVENTION

Traditionally, disposable absorbent articles, such as infant diapers or training pants, adult incontinence products and other such products, are constructed with a moisture-impervious outer backing sheet (or "backsheet"), a moisture-pervious body-contacting inner liner sheet (or "topsheet"), and a moisture-absorbent core (or "absorbent core") sandwiched between the liner sheet and the backing sheets. These disposable absorbent articles oftentimes include additional features such as elastic waist bands, elastic leg bands, and stretchable side panels. Further, decorative graphics can be incorporated into the disposable absorbent article for aesthetic and functional purposes.

Disposable absorbent articles are generally assembled on an automated production line by separately supplying the individual components of the absorbent article to the production line at predetermined locations along the machine direction, and layering the individual components to form an integrated absorbent article. Various methods are available for bringing these individual components together so that the components in the integrated product are in a desired relation with respect to each other. In bringing these individual components together, various known methods have been used to sense the position of a particular component, and then to adjust the placement of subsequent components in order to properly position them with respect to the previously sensed component.

Prior art methods for assembling components of absorbent articles have employed photo/optical techniques to sense reference markers on the individual components. The reference markers assist in cutting and placing the individual components onto the integrated absorbent article. The reference markers have typically been included in the final assembled product. This is so because the reference markers employed in prior techniques need to be sensed downstream in the production line to provide error correction, requiring complex feed-back control systems. However, the inclusion of the reference markers on the final assembled product can detract from the aesthetics of the product and are therefore not desirable.

For example, U.S. Pat. Nos. 5,286,543 and 5,235,515 to Ungpiyakul et al. disclose a system for selectively providing predetermined segments of web material to an absorbent article production line using a reference marker which is incorporated into the final assembled absorbent article. Generally stated, the method includes the steps of supplying the web material at a web speed and sensing a reference mark on the web material to generate at least one reference mark datum which is associated with a selected web segment. A separation datum is provided and the web material is divided along a separation region during production of the web segment. A relative phasing between the sensing of the reference marker and the dividing of the web material is controlled. The phase control is conducted with respect to a set reference value. The web segment is placed onto a substrate, and a location of the separation region relative to the reference mark is separately detected to generate at least one location datum. The location datum is evaluated to generate an updated set reference value, and the phase controlling step is adjusted to incorporate the updated set reference value.

The '543 Patent discloses that the predetermined segments of web material comprise discrete graphic patches corresponding to the tape landing zone of the diaper. The patch is said to have a predetermined set of graphics which are "congruously entire." The patches are also said to abruptly change from graphics set to graphics set and, therefore, from diaper to diaper because there is no modulating transition between the adjacent compositions formed on the original supply roll of web material. The patches are said to be provided with reference markers delineating the boundaries between individual web or patch segments. The reference markers comprise any signaling mechanism which is recognizable by a machine.

During the production of the absorbent article according to the '543 Patent, a first sensing means detects the reference marker associated with the graphic as the web containing the graphics is unwound. Then, at a remote position in the manufacturing process, a second sensor observes the portions of the reference markers which remain upon each web segment. If the web segment is not correctly cut, the remote, second sensor detects this improper separation of the graphic. In order to correct for any improper cutting of the web segment, the system in the '543 Patent generates an updated set reference value based on where the second, remote sensor observes the reference marker downstream in the manufacturing line. The system is then selectively adjusted to incorporate the updated set reference value to assure that subsequent relatively smaller patches of web material are properly cut and positioned with respect to the other components forming the absorbent article.

The '543 Patent at col. 14, lines 24–55 admits to be distinguishable from so-called "conventional techniques" employing, for example, a "shift register" scheme, for matching detector information to a particular manufacturing operation, such as the operation of a cutter. The so-called conventional techniques are said not to be capable of withstanding severe process disturbances. These disturbances, described as start-ups, splices within various web materials, and non-uniform stretching of web material caused by a non-uniform winding of the web materials onto the associated supply roll, are said to cause an improper placement of a significant number of patches and thereby increase cost and waste.

To overcome process disturbances, the so-called conventional techniques discussed in the '543 Patent are said to be sensitive to the distance between the sensing means for detecting the reference marker and the cutting mechanism. In other words, the reference marker sensor in the conventional techniques had to be placed relatively closely to the cutting mechanism because, if for example, a detector is mounted a relatively large distance, such as 25 web segment lengths before the cutting unit, the phasing mechanism can phase 25 patches too soon. Where a new roll of material is spliced onto an expiring roll with the sets of patch graphics on the new roll being "out of phase" from the previous roll, up to 25 patches may be cut incorrectly. Furthermore, the '543 Patent states that conventional techniques in which the detector is mounted a large distance from the cutter, the individual sets of print design graphics may not be exactly equally spaced, and the relative position of the patch graphics measured at the detector may not accurately represent the relative position of the patch graphics when the web material reaches the cutting mechanism. Due to this, the '543 Patent recognizes that the greater the distance between the detector and the cutting mechanism, the larger the errors can be.

To eliminate these processing errors in the situation where the sensor and the cutting mechanism are remote from one another, the '543 Patent employs feedback control in a manner where the reference marker (i) is not removed following its initial sensing by the first sensor, and (ii) is applied to the final assembled absorbent article for subsequent reading by the second, remote sensor. Consequently, the reference marker in the '543 Patent, by virtue of being on the final absorbent article, is constructed to provide for a selected separating of discrete graphics. Indeed, without the reference marker on the final absorbent article in the '543 Patent, feedback control is effectively eliminated from the system described in the '543 Patent, and concomitantly process disturbances evidently will be permitted to cause the improper cutting and/or placement of the graphic, leading to a graphic which is neither aesthetically pleasing nor congruously entire.

Thus, the reference marker portions that remain upon each patch of web material in the final article of the '543 Patent are "constructed to provide for a selected separating" of the graphic sets by enabling both the upstream first sensor and the downstream second sensor to detect the location of the reference marker portion and thereby register and control the location and cutting of the predetermined graphic sets. A claimed aspect of the invention of the '543 Patent is the use of the reference marker portions to provide for the "selected separating" of the graphic sets. This "selected separating" employs an automated registration and "set point error" correction control loop using feedback from the second sensor. The second sensor detects the reference marker portions located on the patches of web material to enable the feedback control and thereby "provide for a selected separating" of the graphic sets.

But even though the so-called conventional techniques described in the '543 Patent do not employ the reference marker later in the process line, they still apparently leave the reference marker on the final, assembled absorbent article. As noted previously, the reference markers in some instances are aesthetically displeasing, so leaving them on the final assembled absorbent article can detract from the presentation of the article.

Similarly, U.S. Pat. No. 5,766,389 to Brandon et al. discloses a process for controllably registering a plurality of components of a continuously moving first layer with a plurality of reference marks on a continuously moving second layer with pre-printed graphics. Brandon's registration process comprises the steps of (1) providing a continuously moving first layer having a plurality of components thereon, (2) providing a continuously moving second layer having a plurality of reference marks thereon, (3) sensing the distance between two successive reference marks, (4) generating a signal in response to the sensed distance, (5) adjusting the distance between subsequent successive reference marks to a selected distance, (6) joining the continuously moving first and second layers together, (7) sensing the position of each reference mark relative to its associated component, (8) generating a signal when one of the reference marks is out of position relative to its component, (9) processing the signal in accordance with preprogrammed instructions to generate a speed command signal, and (10) adjusting the speed of the continuously moving second layer in response to the speed command signal in accordance with preprogrammed instructions.

According to these prior methods, the assembled absorbent article must contain the sensed reference marker(s) to properly enable the complex feed-back control systems of the registration process. The inclusion of the reference marker(s) in the assembled product can detract from the aesthetic qualities of the final absorbent article, and the feed-back control can overly complicate the production line. For example, Procter & Gamble's Pampers® Baby-Dry (tape closure system) and Pampers(® Rash Guard™ (hook and loop closure system) diapers include a reference marker on the closure landing systems, which apparently assists in cutting and placing the graphic on the assembled absorbent article. This marker is visibly apparent in the final assembled product, and detracts from the graphic on the tape landing zone. Further, the assembly and layering of the component parts in the machine direction, as shown in the prior art, limits the flexibility of the production line to incorporate a variety of different graphics into the integrated absorbent article.

These and other disadvantageous features of the prior art are overcome by the invention according to the preferred embodiments.

SUMMARY OF THE INVENTION

In response to the discussed difficulties and problems encountered in the prior art, a disposable absorbent article having a registered graphic and a process therefore has been discovered.

In a first aspect, the present invention provides a method for making absorbent articles, wherein each absorbent article comprises an appliqué layer and the appliqué layer includes a graphic. The method according to the first preferred embodiment comprises the steps of: (a) providing a continuously moving central absorbent pad, a continuously moving topsheet layer, and a continuously moving liquid impermeable backsheet layer; (b) forming a continuously moving absorbent core assembly by layering the continuously moving central absorbent pad between the continuously moving topsheet layer and the continuously moving liquid impermeable backsheet layer, and securing the continuously moving absorbent core assembly together, wherein the continuously moving absorbent core assembly is traveling in a general machine direction; (c) providing a continuously moving appliqué layer including thereon a plurality of graphics, wherein the continuously moving appliqué layer is traveling in a general machine direction; (d) cutting the continuously moving central absorbent core assembly at predetermined locations to form a continuously moving set of discrete absorbent cores; (e) individually turning each of the continuously moving discrete absorbent cores such that the continuously moving discrete absorbent cores are traveling in a general cross machine direction; (f) attaching the cross-directional continuously moving discrete absorbent cores to the continuously moving appliqué layer such that a graphic corresponds to each of the cross-directional continuously moving discrete absorbent cores; (g) cutting the continuously moving appliqué layer with the attached cross directional continuously moving absorbent cores at a predetermined position between said cross directional continuously moving absorbent cores to form discrete absorbent articles, wherein each absorbent article in the set of absorbent articles has an appliqué layer and the appliqué layer includes a graphic.

In yet another embodiment of the present invention, the graphic included on each of the absorbent articles is different from the graphic included on adjacent absorbent articles in the manufacturing line. In other words, a variety pack of absorbent articles is provided such that, for example, each package of absorbent articles contains anywhere from 3 to 15, and preferably from 5 to 10, distinct repeating graphics in each package.

Another aspect of the present invention pertains to a method for making an appliqué layer, wherein the appliqué layer includes a graphic. The method according to the second preferred embodiment comprises the steps of: (a) providing a first continuously moving layer, a second continuously moving layer, and a cutting means, wherein the first continuously moving layer includes a plurality of graphic and a plurality of corresponding reference markers; (b) sensing the location of the graphic using the reference marker; (c) removing the reference marker used in step (b) to sense location of the graphic; (d) cutting the first continuously moving layer into individual segments between each graphic with said cutting means; and (e) applying each of the individual graphic segments to the second continuously moving layer at a predetermined distance frequency to form the continuously moving appliqué layer.

In a particularly preferred embodiment of the present invention, the graphic is placed on the appliqué layer according to a method comprising the steps of: (a) sensing a fixed phase position of the cutting means and setting a position flag corresponding to the fixed phase position of the cutting means; (b) determining a position encoder count when the position flag is set; (c) sensing the reference marker associated with the graphic, and setting a reference marker flag corresponding to the position of the graphic operatively associated with the sensed reference marker; (d) determining a reference marker encoder count when the reference marker flag is set; (e) determining the relative positional difference between the reference marker encoder count and the position encoder count; (f) comparing the determined relative positional difference to a predetermined set-point value; and (g) adjusting the position of the graphic operatively associated with the sensed reference marker to compensate for any variance between the determined relative positional difference and the predetermined set-point value.

These and other objects, features and advantages of the preferred embodiments will become more readily apparent upon reading of the detailed description of the preferred embodiments of this invention in conjunction with the following drawings.

DETAILED DESCRIPTION OF THE PREFERRED EMBODIMENTS

Figure 1:
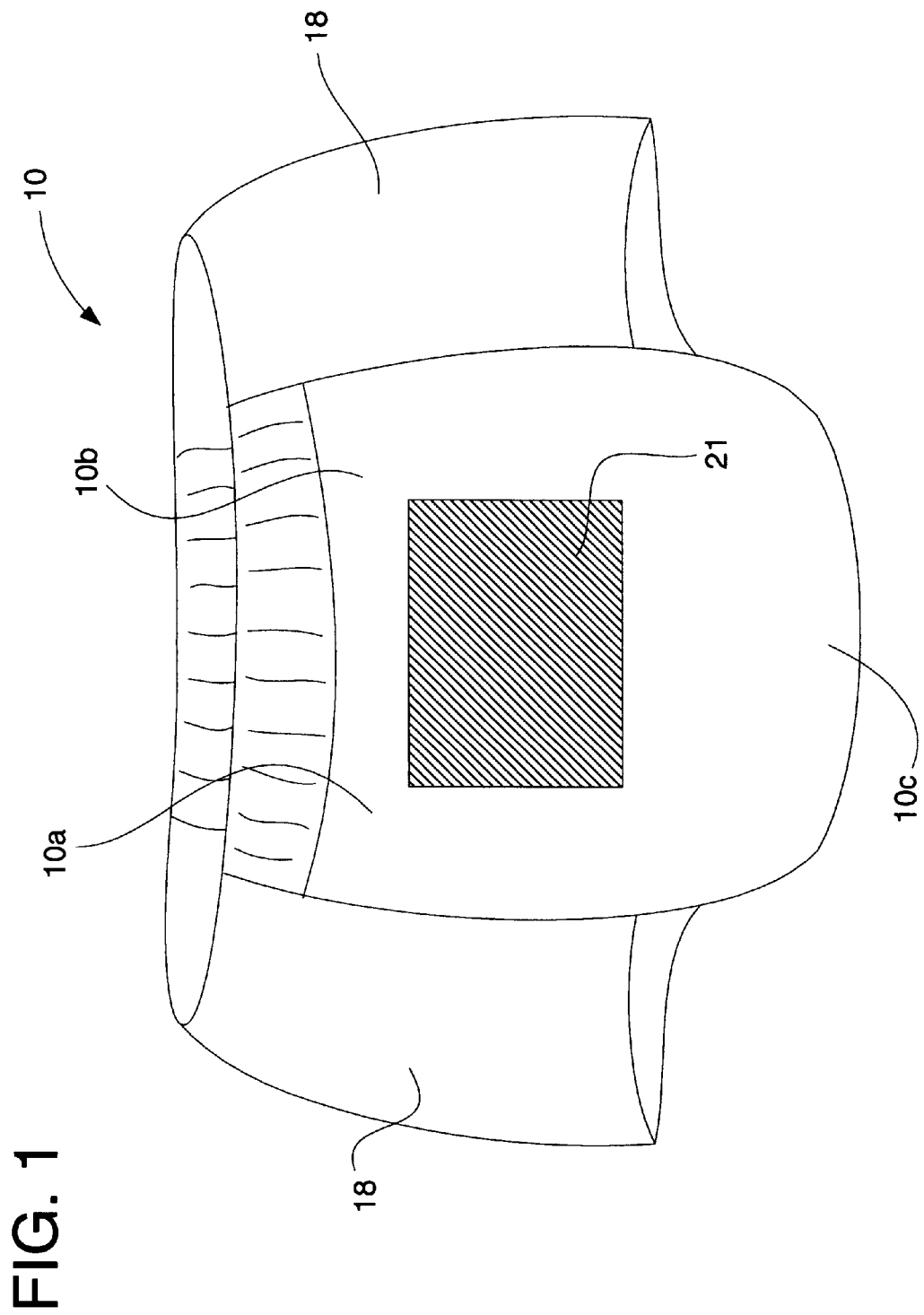
FIG. 1 illustrates a child's training pant with a graphic thereon according to the preferred embodiments.

As used herein, the term "absorbent garment" or "absorbent article" refers to garments that absorb and contain exudates, and more specifically, refers to garments which are placed against or in proximity to the body of the wearer to absorb and contain the various exudates discharged from the body. A non-exhaustive list of examples of absorbent articles includes diapers, diaper covers, disposable diapers, training pants, feminine hygiene products, and adult incontinence products. The term "disposable absorbent garment" refers to absorbent garments that are intended to be discarded or partially discarded after a single use (i.e., they are not intended to be laundered or otherwise restored or reused).

The present invention can be used with all of the foregoing classes of absorbent articles, without limitation, whether disposable or otherwise. These classifications are used interchangeably throughout the specification, but are not intended to limit the claimed invention. The invention will be understood to encompass, without limitation, all classes and types of absorbent articles, including those described above.

The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, indicia or the like.

The following detailed description will be made in the context of sensing and placing graphics in the manufacture of disposable absorbent articles, and specifically a child's training pant. Reference markers used to sense the graphics are removed prior to assembling the absorbent article.

Further, in a preferred embodiment, the absorbent articles are produced by forming a continuously moving absorbent core assembly comprising a variety of components assembled in the general machine direction ("MD"), turning the continuously moving absorbent core assembly to travel in the general cross direction ("CD"), and attaching the CD continuously moving absorbent core assembly to an appliqué layer including a graphic. This method allows for placement of a variety of graphics without the necessity of complex feed-back control systems or the presence of reference marks on the final absorbent article.

The term "machine-direction" or "MD" refers to the primary direction of movement of continuously moving layers in the production line, and the term "cross-direction" or "CD" refers to a direction transverse to the machine-direction.

The present invention provides absorbent articles having graphics accurately cut and positioned with respect to other components of the absorbent article. Examples of graphics include, but are not limited to, indicia highlighting or emphasizing leg and waist openings in order to make product shaping more evident or visible to the user; indicia highlighting or emphasizing areas of the product to simulate functional components such as elastic leg bands, elastic waistbands, and fly openings; indicia highlighting areas of the product to change the appearance of the size of the product; wetness indicators, temperature indicators, fit indicators, and the like; front and/or back labels or pictorials; or written instructions.

Figure 2:
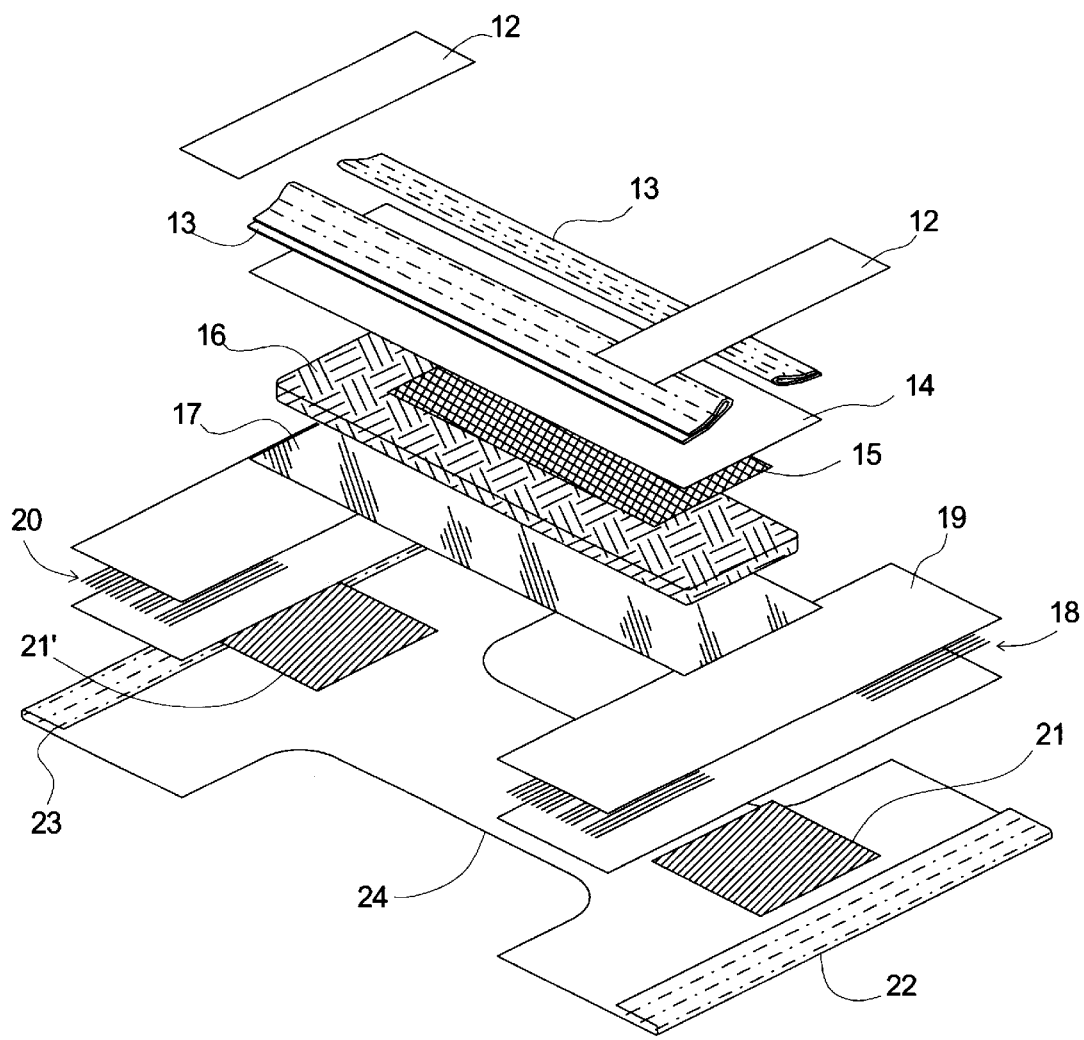
FIG. 2 is an exploded view of the training pant of FIG. 1.

With reference to FIG. 1, an assembled training pant 10 according to the present invention comprises a front waist panel 10a, a rear waist panel 10b opposite the front waist panel 10a, and a crotch portion 10c located therebetween. The training pant 10 is provided with an absorbent core 16 positioned between a liquid impermeable backsheet 17 and a liquid permeable topsheet 14 (as shown in FIG. 2). The training pant further includes an outermost non-woven layer 22 having a cloth-like texture and elastic side panels 18 that are positioned between the liquid impermeable backsheet 17 and the outermost non-woven layer 22 in order to provide elasticity thereto. The liquid impermeable backsheet 17 can preferably be formed from polyethylene, however any suitable material can be used, as is known in the art. The outermost non-woven layer 22 can preferably include at least one graphic 21 positioned thereon. The graphic 21 can be positioned on either the exterior or interior face of the non-woven layer 22. The graphic 21 generally includes a visually pleasing design or pattern and is applied to the absorbent article at a designated area in the final absorbent article 10. In a particularly preferred embodiment, one graphic is positioned on the front waist panel 10a of the final absorbent article, and another aesthetically corresponding graphic is positioned on the rear waist panel 10b.

With continued reference to FIG. 2, the training pant 10 includes an outermost non-woven layer 22, aesthetically corresponding graphics 21 and 21', elastic side panels 18, a liquid impermeable backsheet layer 17, an absorbent core 16, and a liquid permeable topsheet 14. The absorbent core 16 preferably comprises a mixture of cellulosic fibers, such as comminuted softwood pulp fibers, and distributed particles of a superabsorbent polymer (SAP). The pulp/SAP absorbent core is also preferably surrounded by a tissue layer over-wrap (not illustrated) to contain the SAP. However, it should be recognized that any absorbent material known in the art could be used.

The topsheet 14 is preferably made from any suitable material known in the art, including polymeric fabrics such as polyolefin non-woven fabrics. Common polyolefin non-woven fabrics include polypropylene and polyethylene spunbonded fabrics. Additionally, the topsheet of the present invention can be formed from non-woven bicomponent polymeric fabrics.

The training pant can also include a transfer layer 15 adjacent the absorbent core 16, as well as leg gathers 13. Non-woven protector strips 12 are positioned at the longitudinal ends of the leg gathers 13. The elastic side panels 18 preferably comprise a composite of elastic elements 20 and carrier strips 19. During production, the elastic elements 20 extend entirely across the width of the waist opening. However, the elastic elements 20 are cut, causing them to snap back to the side edges of the article corresponding to the area where the elastics have been adhesively attached to the carrier strips 19. In this manner, the elastic elements 20 are positioned and cut such that they do not overlap the graphics 21, 21'. Further, the training pant 10 may optionally include elastic waist elements 23 and elastic leg elements extending along leg openings 24.

Figure 3:
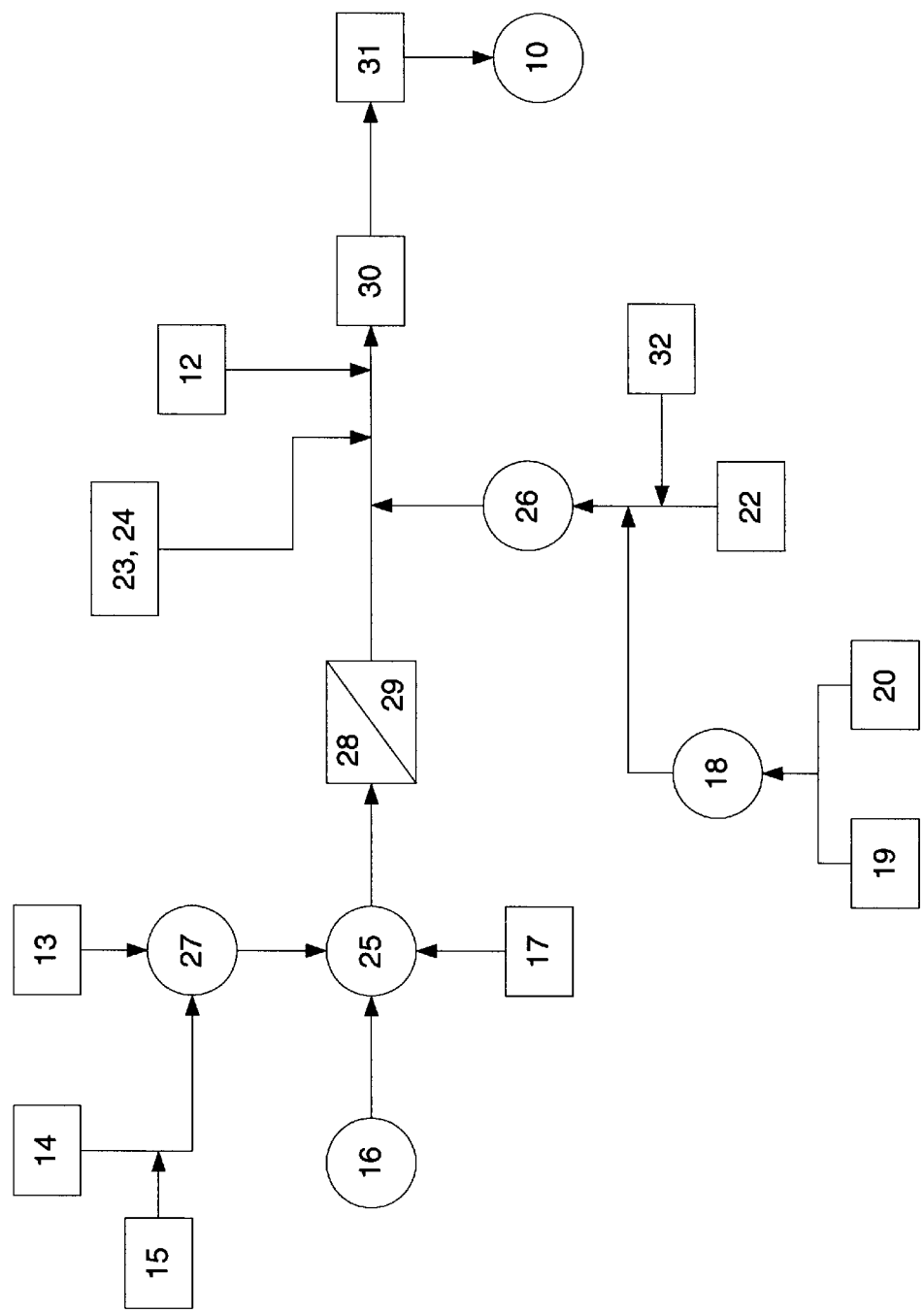
FIG. 3 shows a schematic of a preferred method for making an absorbent article according to the present invention.
Figure 6A:
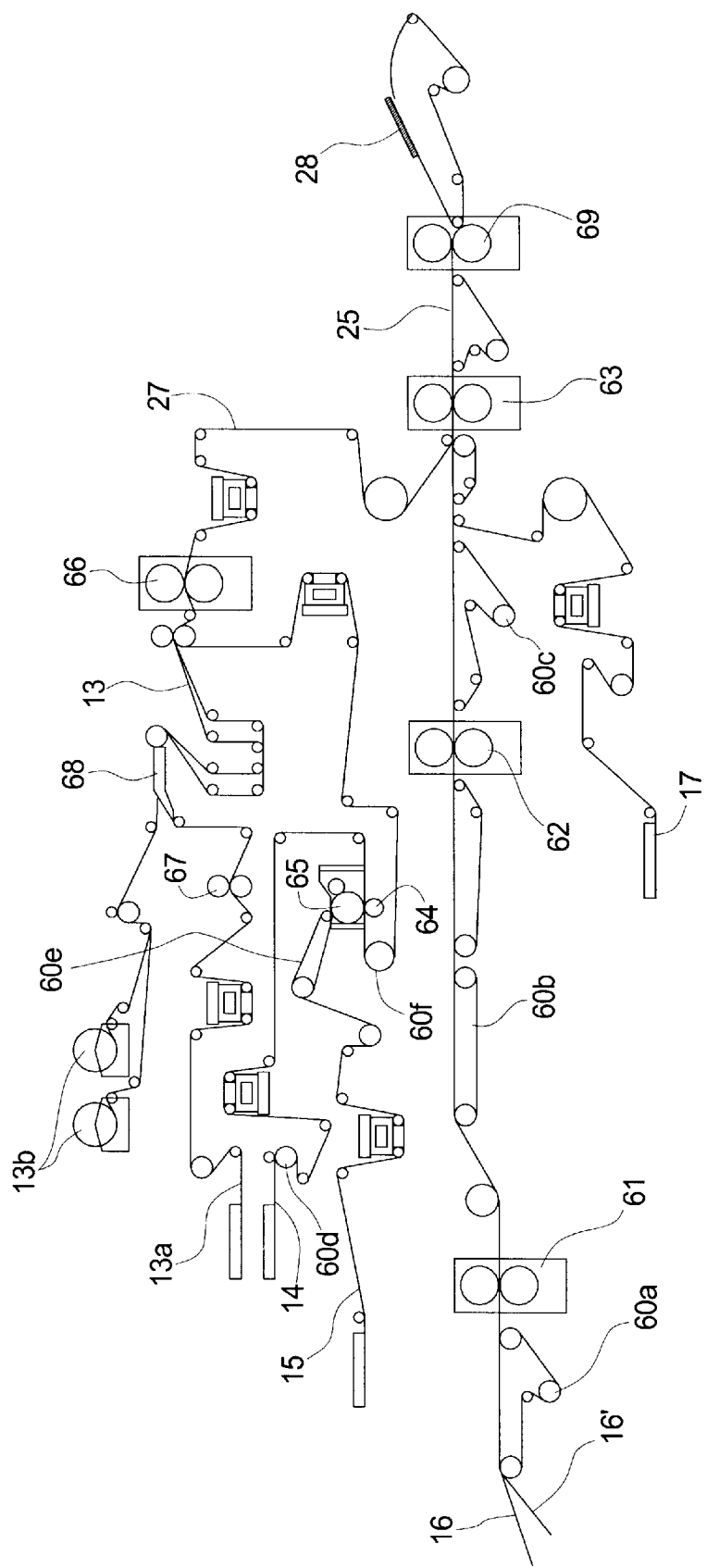
FIGS. 6A–6C show a schematic of a particularly preferred manufacturing line for practicing the invention according to the preferred embodiments.

The absorbent articles of the present invention can preferably be produced according to the system schematically illustrated in the flow diagram of FIG. 3. Generally stated, the method includes the steps of forming an absorbent core assembly 25 and an appliqué layer 26 in the general machine direction; turning the absorbent core assembly 25 to travel in the general cross direction, attaching the absorbent core assembly 25 moving in the general cross direction to appliqué layer 26; and cutting the joined assembly to form discrete absorbent articles 10. The absorbent core assembly 25 can include a central absorbent pad or core 16 comprising a pulp/SAP absorbent pad wrapped in tissue 16' (FIG. 6A). The absorbent pad 16 can be continuously formed in a manufacturing line by any method known in the art, such as through the deposition of fluff and SAP on a drum-type air forming apparatus.

The absorbent core assembly 25 can further include a topsheet assembly layer 27 and a liquid impermeable backsheet layer 17. The absorbent core assembly 25 can be continuously produced by providing a MD continuously moving absorbent core 16, a MD continuously moving topsheet assembly layer 27, and a MD continuously moving liquid impermeable backsheet layer 17; layering the absorbent core 16 between the topsheet layer 27 and the backsheet layer 17; and securing the layers together to form the absorbent core assembly 25. As such, the components are provided, layered, and secured in the general machine direction.

The topsheet assembly layer 27 can include a non-woven topsheet layer 14, a transfer layer 15, and leg gathers 13. The topsheet assembly layer 27 can be continuously produced by providing a MD continuously moving transfer layer 17, a MD continuously moving non-woven topsheet layer 14, and a pair of MD continuously moving leg gathers 13; layering the topsheet layer 14 on top of the transfer layer 15; securing the layers together; and attaching the leg gathers 13 to the side edges of the topsheet layer 14 on the side opposite the transfer layer 15 to form the topsheet assembly layer 27. Again, the components are provided, layered, and secured in the general machine direction.

The MD continuously moving discrete absorbent cores 28 are then individually turned at step 29 to travel in a general cross direction. These CD continuously moving discrete absorbent cores 28 are joined with an appliqué layer 26, sealed at step 30, and cut at step 31 at predetermined locations to form discrete absorbent articles 10. Elastic waist elements 23, elastic leg elements 24, and non-woven protector strips 12 can also be applied at a predetermined location after the appliqué layer 26 has been joined with the CD continuously moving discrete absorbent cores 28.

Figure 4A:
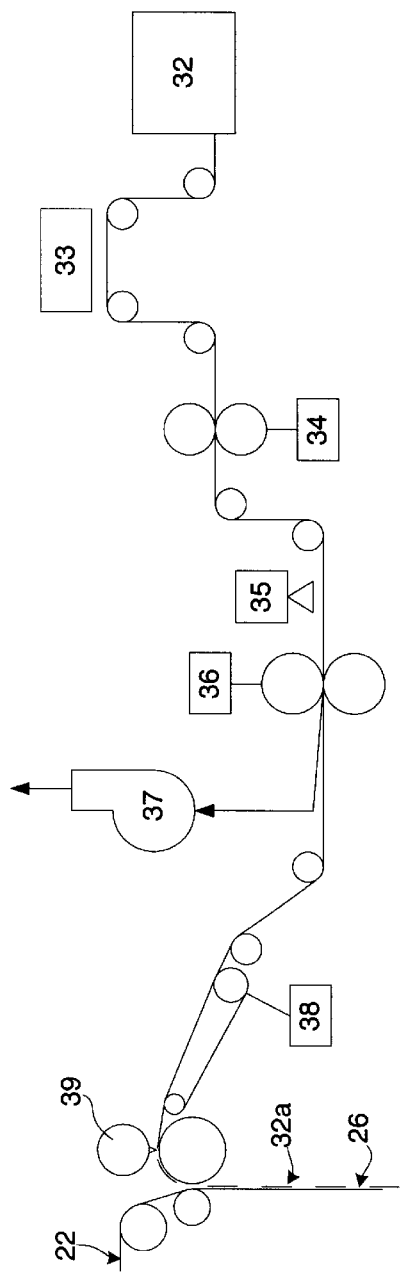
FIGS. 4A–4B show a schematic of a preferred method for placing a graphic on an absorbent article.

As described above, an absorbent article produced according to the present invention does not have a reference marker 21a (see FIG. 5) corresponding with the graphic 21 on the final absorbent article 10. Unlike U.S. Pat. No. 5,286,543 and other similar prior art with complex feedback control mechanisms, it has been discovered that the graphic (s) 21 can still be properly placed on the final product in an automated manufacturing line without the necessity of including the reference marker(s) 21a on the final product. For instance, the graphic(s) 21 can be placed on the non-woven backsheet 22 without a corresponding reference marker according to the process schematically depicted in FIG. 4a. FIG. 4a shows a method for making an appliqué layer 26 by placing a graphic 21 on a moving non-woven web 22, which forms the backsheet to the absorbent article.

Figure 5A:
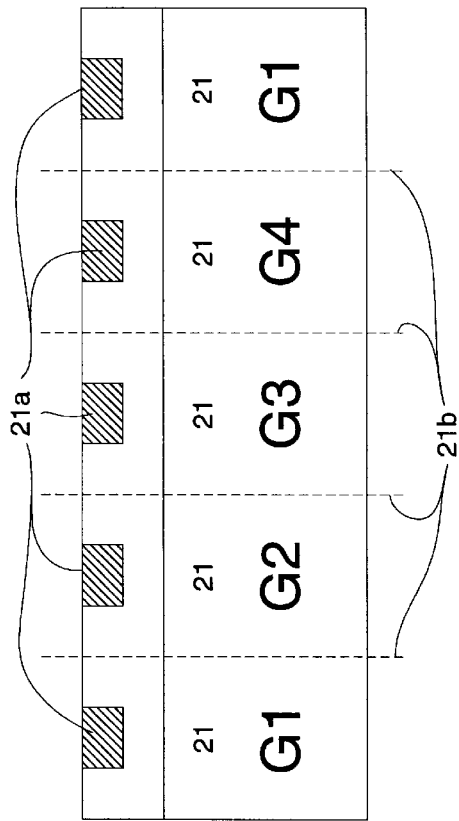
FIGS. 5A–5E illustrate a layer with graphics and reference markers printed thereon preferably used in the methods of FIGS. 3 and 4A–4B.
Figure 5B:
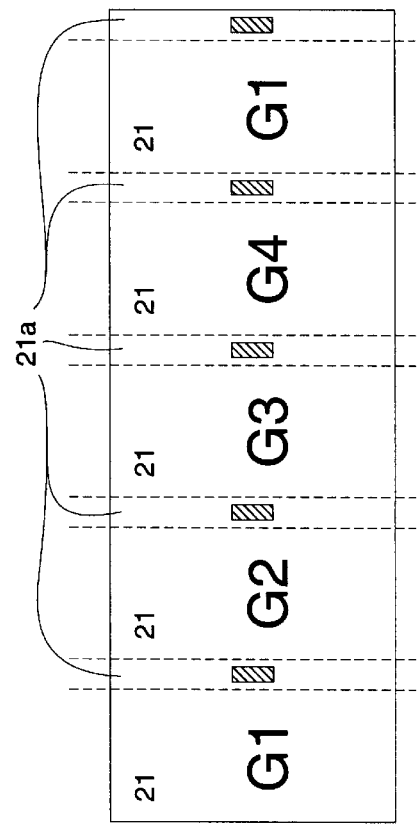

Generally stated, the appliqué layer 26 is preferably formed from an outer non-woven layer 22 which includes a plurality of graphics 21. The graphics 21 are provided from a first MD continuously moving layer or master roll 32, which has a plurality of graphics 21 and a corresponding plurality of reference markers 21a (see FIG. 5A) printed thereon. The graphics 21 and reference markers 21a are positioned relative to one another on the master roll 32 such that at least one reference marker 21a is operatively associated with each of the graphics 21. The graphics 21 and reference markers 21a can be configured in any suitable manner. For example, as shown in FIGS. 5A–5B, the reference markers 21a can be positioned above (FIG. 5A) and/or adjacent (FIG. 5B) the graphic 21 operatively associated therewith.

The appliqué layer 26 can be can be continuously produced by (i) providing a first MD continuously moving layer or master roll 32 including the graphics 21 and reference markers 21a printed thereon, a MD continuously moving second layer or outer non-woven layer 22, and cutting means 39; (ii) sensing the location the reference marker(s) 21a; (iii) removing the reference marker(s) 21a; (iv) cutting the first MD continuously moving master roll 32 into individual segments 32a at locations 21b (as shown in FIGS. 5A–5E) between the graphics 21; and (v) applying each of the individual segments 32a to the MD continuously moving outer non-woven layer 22 at a predetermined distance frequency to thereby form the appliqué layer. Again, the components are provided, cut, and applied in the general machine direction to form the appliqué layer. Further, as mentioned previously, additional components such as elastic side panels 18 can be applied to the appliqué layer 26.

The term "predetermined distance frequency" means that the individual segments 32a are applied to the outer non-woven layer 22 at such a frequency that they are spaced along the length of the appliqué layer 26 an appropriate predetermined distance to allow for the placement of a single graphic 21 on the absorbent article 10. For instance, the individual segments 32a can be spaced along the length of the appliqué layer 26 a predetermined distance that generally corresponds to the width of the absorbent article 10 such that a single individual segment 32a is centered on the front waist panel and/or the rear waist panel of the absorbent article 10, as depicted in FIGS. 1 and 2.

As shown in FIG. 4A, in a particularly preferred embodiment of the present invention, the continuously moving master roll 32 is conveyed by conveyor 34. A web guide 33 centers the master roll 32 on conveyor 34. A photo-eye or optical sensor 35 detects the reference markers 21a. The reference markers 21a can include an optical brightener, or can be configured as a color bar which the photo-eye or optical sensor 35 can detect. However, it should be understood that any suitable method known in the art can be used to "sense" the reference markers 21a.

Figure 5D:
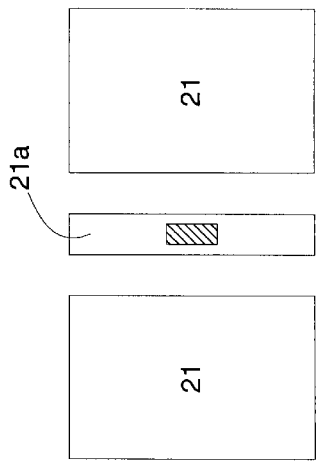
Figure 5C:
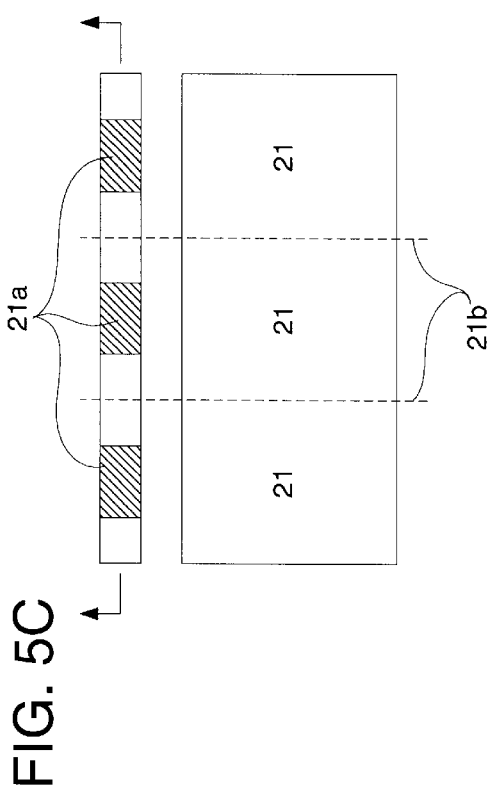

Once the reference markers 21a have been sensed or detected, they can be removed by any suitable means. A slitter 36 separates the reference markers 21a from the remainder of the master roll 32 (as shown in FIGS. 5C–5D). A vacuum pump 37, or other suitable means, then removes the reference markers 21a from the remainder of the master roll 32.

Once the reference markers 21a are removed, the master roll 32 (without any reference markers whatsoever) is conveyed forward by servodrive 38 to cutting means 39. At cutting means 39, master roll 32 is cut at predetermined locations 21b to form individual segments 32a, which are then applied to non-woven outer layer 22 to form appliqué layer 26. The cutting means 39 can be any means known in the art. In a particularly preferred embodiment, the cutting means 39 comprises a manually phased cutting knife and vacuum transfer drum.

As described in more detail below, and unlike the process described in U.S. Pat. No. 5,286,543, a manually phased cutting knife 39 can preferably be used in conjunction with sensor 35 to cut the master roll 32 at predetermined locations 21b without the need for complex feedback control systems. Generally, the phasing of cutting means 39 can be manually set, and servodrive 38 can control the speed at which the master roll 32 is conveyed based on a comparison of the phase of cutting means 39 and predetermined manufacturing line parameters such as the distance between sensor 35 and cutting means 39. Such a configuration only relies on simple feed-forward control. The present invention is able to employ feed-forward control, because cutting means 39 is preferably located along the manufacturing line in relatively close proximity to sensor 35 so that error is minimized. As such, the necessity for complex feed-back control as disclosed in U.S. Pat. No. 5,286,543 is eliminated.

In yet another embodiment of the present invention, master roll 32 can be formed from a sticker base wherein the graphics 21 are located on the "sticker" portion of the master roll 32, and the reference markers 21a are located on the "backing" portion of the master roll 32. In such a configuration, once the reference marker 21a is detected, the sticker portion including the graphic 21 can be removed from the backing portion including the reference marker 21a. The sticker portion can then be applied to the non-woven outer layer 22 and the backing portion can be discarded.

As mentioned above, the resulting absorbent article can preferably include at least two graphics thereon—one on the front waist panel and another on the rear waist panel. The graphics on the front and rear waist panels preferably aesthetically correspond to each other. The term "aesthetically correspond" means that the graphics pictorially interrelate to one another. For instance, the graphics can depict a scene from both the front perspective and the rear perspective. Such an absorbent article can be produced by the method shown in FIG. 4B using a master roll 32 as depicted in FIG. 5E.

Figure 4B:
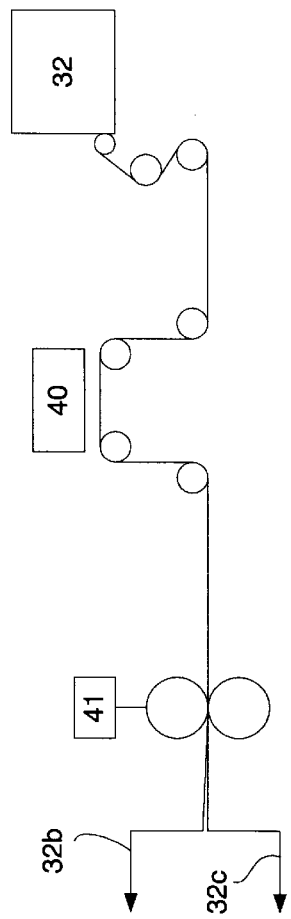
Figure 5E:
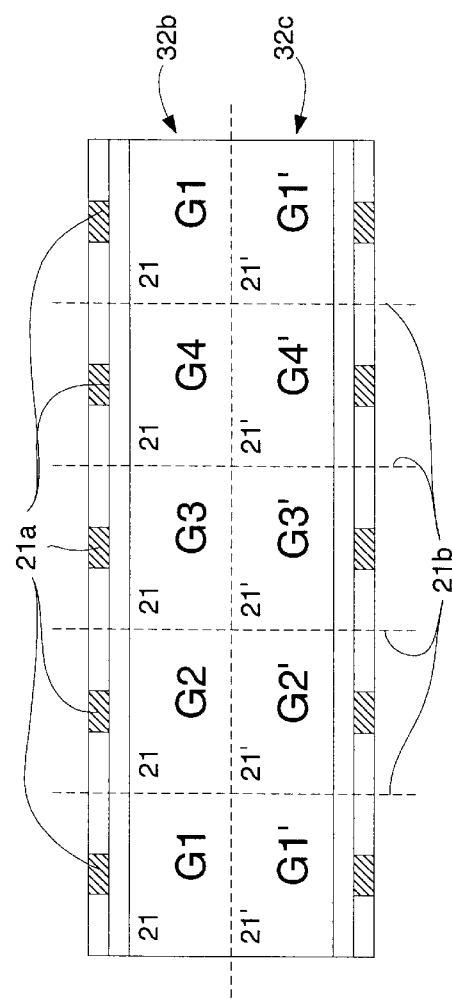

FIG. 5E shows a master roll with aesthetically corresponding graphics 21 and 21'. As shown in FIG. 4B, the master roll 32 can be conveyed through web guide 40 and separated into two separate master rolls 32b and 32c by slitter 41. Each separate mater roll 32b, 32c can then be separately placed on the non-woven backsheet 22 according to the method depicted in FIG. 4A. Preferably, the individual segments 32a obtained from the separate master rolls 32b and 32c can be applied to the outer non-woven layer 22 at opposite ends thereof (see elements 21, 21' in FIG. 2) to result in an appliqué layer 26 with two aesthetically corresponding graphics 21 and 21' located opposite each other.

Figure 6B:
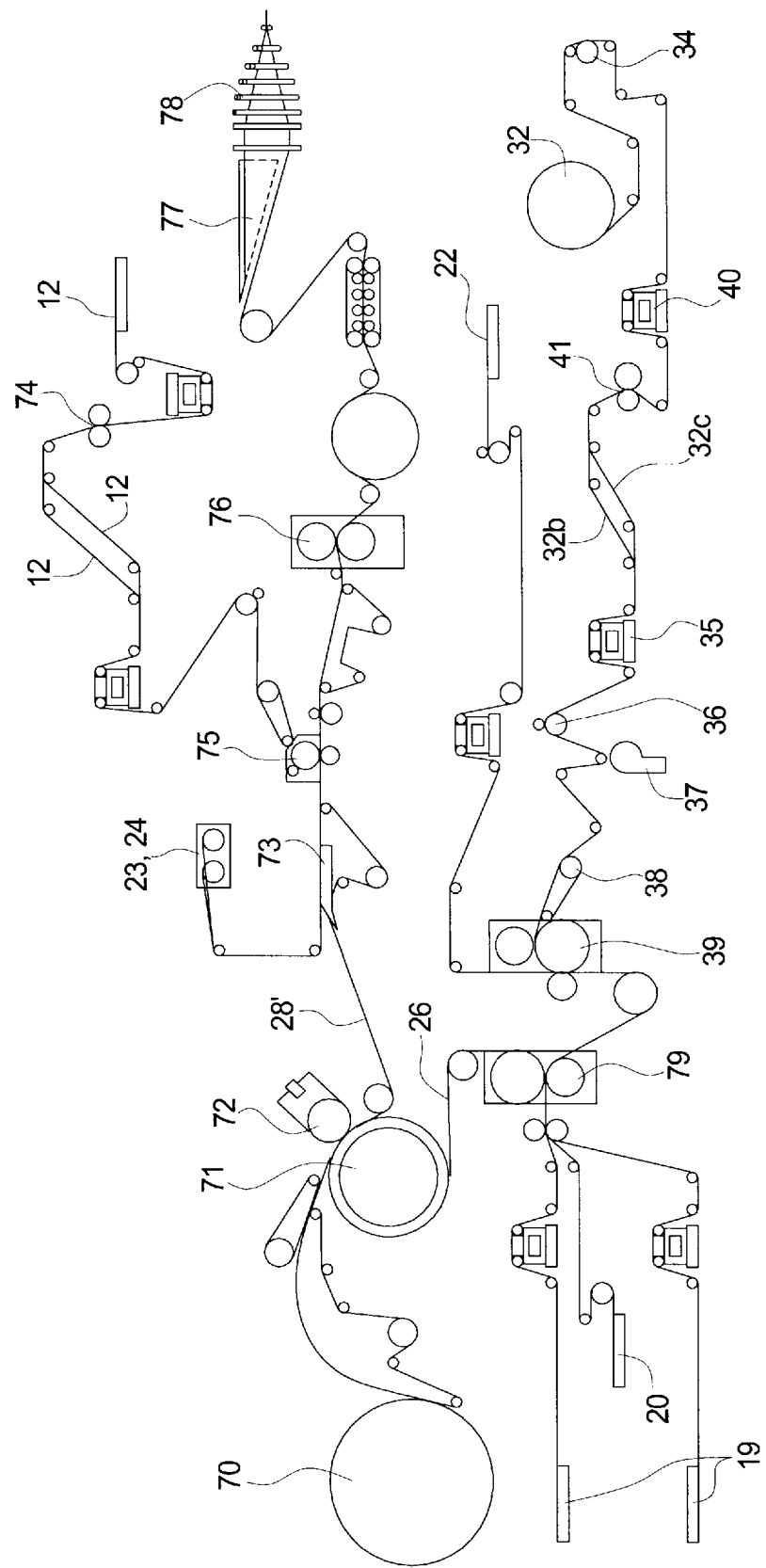
Figure 6C:
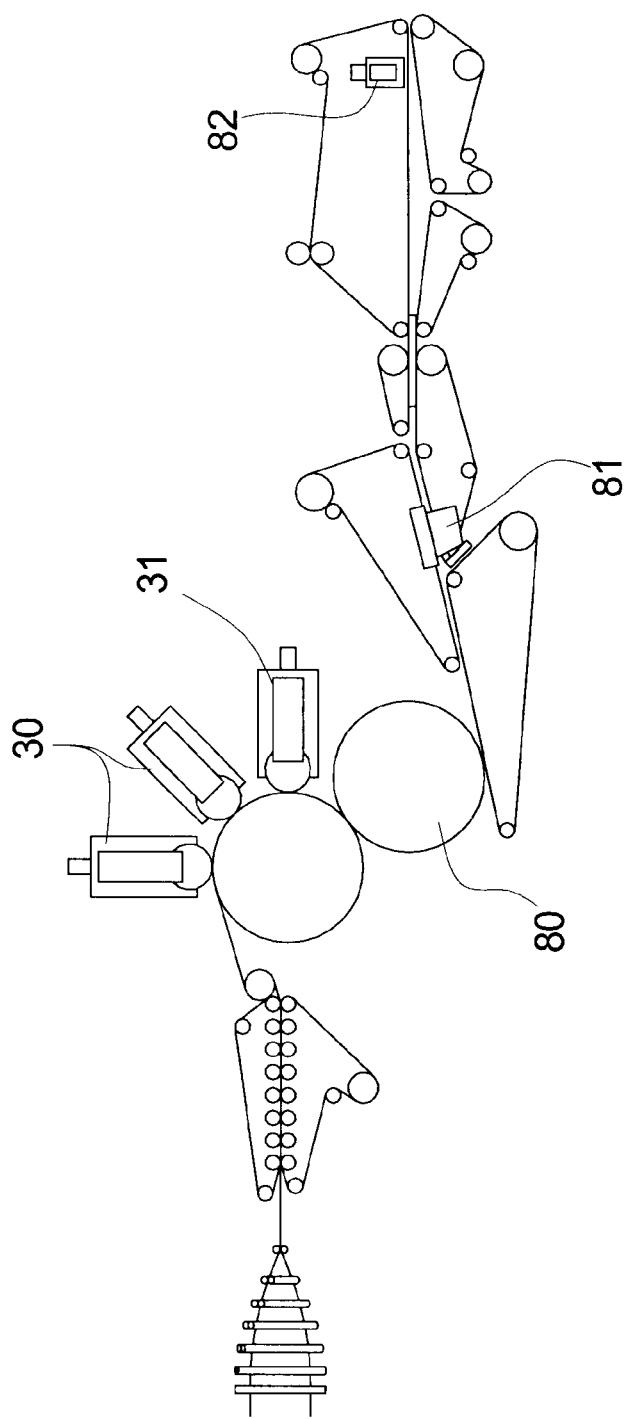

In a particularly preferred embodiment of the present invention, the absorbent articles can be produced in an automated manufacturing line as depicted in FIGS. 6A–6C. Specific mechanisms are provided along, and as part of, the manufacturing line for engaging, conveying, acting against, or otherwise operating on, or relative to, at least one component of the absorbent article being formed.

The mechanisms in the manufacturing line for operating on, or relative to, a component of the absorbent article may include special or conventional mechanisms. The details of such mechanisms, and the detailed method of operation of such mechanisms, will be apparent to those having skill in the art and the detailed descriptions of such mechanisms are not necessary to an understanding of the invention. However, a brief description of the location and purpose of some of the mechanisms is presented to serve as examples of the types of mechanisms with which the present invention may be employed as described in detail hereinafter.

Referring first to the left-hand end of FIG. 6A, a central absorbent pad 16 is introduced into the manufacturing line. The central absorbent pad 16 can be a continuous web supplied from a suitable bulk roll supply (not illustrated). In other modes of operations, a pocket former or drum former (not illustrated) may be provided upstream of the manufacturing line to form individual, and optionally contoured, central absorbent pads 16 of blown, non-woven fluff material. Optionally, the pads 16 may be impregnated with superabsorbent polymer to increase the absorbent capacity of the pads 16. The pads can then be conveyed seriatim in a spaced array through the manufacturing line.

The individual central absorbent pads or the continuous, central absorbent pad 16 are conveyed down the manufacturing line (toward the right as viewed in FIG. 6A) by conveyor 60a. A vacuum hold-down system (not illustrated) may be provided along the conveyor 60a, and along other conveyors in the manufacturing line, to maintain the components flat and to center the components so as to provide for proper placement of the various components during the manufacturing operations. The mechanical and structural details per se of the conveyor, of the vacuum system, and of other similar conveyors and vacuum systems in the manufacturing line are generally known in the art.

As mentioned previously, central absorbent pad 16 can be wrapped with a tissue layer; As illustrated in FIG. 6A, the tissue wrap 16' can be provided from a supply roll (not shown), wrapped around the central absorbent pad 16, and the wrapped absorbent pad can then be fed through a debulker 61 to compress the tissue and absorbent pad. The supply roll, debulker, motor-driven unwind mechanisms, and other associated mechanisms operate in a conventional manner.

The compressed absorbent pad 16 is moved forward from the debulker 61 by a draw conveyor 60b to a pad knife mechanism 62 which severs the central absorbent pad 16 at intervals to provide separate absorbent pads. The separate absorbent pads are conveyed downstream of the knife mechanism 62 by a spacing conveyor 60c, which has a linear speed greater than the linear speed of the draw conveyor 60b so as to separate the individual absorbent pads and provide a desired end-to-end spacing.

The spacing conveyor 60c feeds the spaced-apart absorbent pads to a heat sealer 63 where the liquid impermeable backsheet layer 17 and the topsheet assembly layer 27 are combined with the absorbent pads 16. The backsheet layer 17 and topsheet assembly 27 are fabricated and partially assembled in other mechanisms in the machine as will next be explained.

As stated previously, the topsheet assembly layer 27 is formed from a non-woven topsheet layer 14, a transfer layer 15, and leg gathers 13. The topsheet 14 is provided from a supply roll (not shown), fed by conveyor 60d, and joined with transfer layer 15 at drum 64. Transfer layer 15 is provided from a supply roll (not shown), fed by conveyor 60e through cutter 65, and joined with topsheet 14 at drum 64. The joined transfer layer 15 and topsheet 14 are then fed by conveyor 60f to sealer 66 where the leg gathers 13, the topsheet 14, and the transfer layer 15 are all joined together to form the topsheet assembly 27.

The leg gathers 13 are formed from leg gather sheet 13a and leg gather elastics 13b. The leg gather sheet 13a is fed through slitter 67 to form two discrete leg gather sheets. Leg gather elastics 13b are fed forward and joined with the two discrete leg gather sheets. The joined elastics and leg gather sheets are then fed through folder 68 to form leg gathers 13. The leg gathers 13 are then fed through sealer 66 where the topsheet assembly 27 is formed. The leg gather elastics 13b are secured to the leg gather sheets by a conventional device that (1) provides a continuous length of elastic 13b along the sheets 13a, (2) separates the elastic into a plurality of continuous, substantially parallel filaments, and (3) tensions the elastic filaments as the elastic filaments are fed against the leg gather sheets 13b.

The liquid impermeable backsheet layer 17 is initially supplied in the form of a continuous backsheet web from a backsheet web supply roll (not shown). The supply roll and associated operating mechanisms operate in a conventional manner.

The backsheet layer 17, topsheet assembly 27, and absorbent pads 16 are fed forward to sealer 63 where the backsheet layer 17 is then attached to (1) the separate absorbent pads and (2) the portions of the top sheet assembly layer 27 which extend beyond the separate absorbent pads. The completed topsheet assembly 27 is drawn through sealer 63 and attached with the absorbent pads 16 and underlying backsheet layer 17. All of the component pieces of the absorbent core assembly 25 are assembled in the proper relationship at sealer 63. Once the absorbent core assembly 25 is formed, the MD continuously moving absorbent core assembly 25 is fed through cutter 69 and cut at predetermined locations to form MD continuously moving discrete absorbent cores 28.

With reference to FIG. 6B, the MD continuously moving discrete absorbent cores 28 are then transferred onto turn drum 70 and rotated approximately 90° to travel in the general cross direction (CD). Once turned, the CD continuously moving discrete absorbent cores 28 are transferred onto assembly drum 71, where they are joined together with appliqué layer 26 and sealed by end side sealer 72 to form sealed assemblies 28'.

It should be noted that when the appliqué layer 26 is joined together with the CD continuously moving discrete absorbent cores 28 and sealed to form the sealed assemblies 28', the non-woven carrier strips 19 (FIG. 2) including the discrete elastic side panels 18 (described in more detail below) are continuous and thereby interconnect the individual discrete absorbent core assemblies 28 in the sealed assemblies 28'.

With reference to the right side of FIG. 6B, the fabrication of appliqué layer 26 is illustrated. First, the continuously moving master roll 32, including a series of aesthetically corresponding graphics 21 and 21' (see FIG. 5E), is fed through web guide 40 by conveyor 34. Once centered by web guide 40, master roll 32 is fed through slitter 41, where it is separated into two separate master rolls 32b and 32c.

Each separate master roll 32b, 32c can then be identically processed according to the preferred method described herein. However, for ease of reference, only the processing of separate master roll 32b will be described with the understanding that master roll 32c is processed similarly.

Master roll 32b is conveyed past photo-eye/web guide 35, where the location of reference markers 21a (see FIG. 5E) are sensed. Once the reference markers 21a have been sensed, master roll 32b is fed through slitter 36, where reference markers 21a are separated from master roll 32b and removed by vacuum pump 37. Master roll 32b is then conveyed by servodrive 38 through appliqué cutter 39, where master roll 32b is cut into individual segments 32a (see FIG. 4A) at predetermined locations 21b (see FIG. 5E). Individual segments 32a are then applied to non-woven outer layer 22 at appliqué cutter 39 to form a graphic-containing non-woven layer 26. Again, it is emphasized that reference markers 21a are removed from master roll 32b prior to the formation of the individual segments 32a and prior to the formation of the graphic containing non-woven layer. This is possible because of the close proximity of photo-eye 35, and appliqué cutter 39. In other words, because photo-eye 35 and appliqué cutter 39 are near one another, the reference markers 21a may be removed from the master roll web 32b prior to placement of the individual segments 32a onto the non-woven outer layer 22. In the prior art such as the '543 Patent, in the event the cutting and placing operation occurs at greater distances, feedback control becomes necessary to assure that the appliqué is properly positioned with respect to the other components of the absorbent article. The non-woven outer layer 22 is then provided from a continuous supply roll (not shown). The non-woven outer layer 22 supply roll and associating operating mechanisms operate in a conventional manner.

The graphic containing non-woven layer is then conveyed forward and joined with discrete elastic side panels 18 at elastics cutter 79.

With reference to the left side of FIG. 6B, discrete elastic side panels 18 are formed from carrier strips 19 and side panel elastic elements 20 (see also FIG. 2). The carrier strips 19 and side panel elastic elements 20 are provided from continuous supply rolls (not shown). The carrier strips 19 are conveyed forward and joined with side panel elastic elements 20 using conventional placement techniques. The joined elastic/carrier strip assembly is then fed through elastics cutter 79, where the side panel elastic elements 20 are cut along a longitudinal centerline to form discrete elastic side panels 18, and the discrete elastic side panels 18 are joined with the graphic-containing non-woven layer to form appliqué layer 26. It is noted that the side panel elastic elements 20 are cut along a longitudinal centerline such that they "snap back" to provide elasticity to the side portions of the appliqué layer 26, while leaving the center portion unelasticized (see FIGS. 1 and 2). The appliqué layer 26 is then conveyed forward and joined together with the CD continuously moving discrete absorbent cores 28 to form the sealed assemblies 28', as described above.

Once appliqué layer 26 is joined with the CD continuously moving discrete absorbent cores 28 and sealed to form sealed assemblies 28', waist and optionally leg elastic elements 23 and 24 are applied to the peripheral edges of the sealed assemblies 28'. The waist and optional leg elastic elements 23 and 24 are provided from a continuous supply of elastic strands (not shown) and placed on the sealed assemblies 28' using conventional placement techniques. The waist edges of the sealed assemblies 28' are then folded over the waist elastic elements 23 by waist folder 73.

Non-woven protector strips 12 are then applied to the sealed assemblies 28'. The non-woven protector strips 12 are supplied from a continuous roll of non-woven web (non shown). The supply web is cut into separate left and right side protector strips 12 at slitter 74. The individual protector strips 12 are then cut by cutter 75 at a predetermined location, conveyed forward and joined with sealed assemblies 28'.

Once the non-woven protector strips 12 are applied to the CD continuously moving discrete sealed assemblies 28', the sealed assemblies 28' are conveyed forward and fed through leg hole cutter 76, where the side edges of the sealed assemblies 28' are trimmed to provide appropriate leg hole openings. The CD continuously moving discrete sealed assemblies 28' are then folded along the lateral centerline of the individual assemblies by bi-folder 77 to orient the CD continuously moving discrete sealed assemblies 28' such that the front waist portions 10a and rear waist portions 10b oppose each other.

The folded assemblies 28' are then rotated 90° at twist-conveyor 78 and, with reference to FIG. 6C, conveyed to heat seal unit 30 where the side edges of the folded assemblies 28' are sealed to complete the formation of the elastic side panels 18 (as shown in FIG. 1). Once the side edges are sealed, the assemblies are passed through final cutter 31 to form individual absorbent articles 10. The sealed assemblies 28' are separated into individual absorbent articles 10 at final cutter 31 by severing the continuous non-woven carrier strips 19 interconnecting the discrete absorbent cores 28 at predetermined locations between each of the discrete absorbent cores 28. The placement and cutting of the sealed assemblies 28' are accomplished using conventional registration and placement methods.

The individual absorbent articles 10 are then transferred to drum 80 and conveyed to rejector 81 where the individual absorbent articles 10 are monitored for quality. The final absorbent articles 10 conforming with quality checks are then conveyed to tack hold 82 for packaging.

According to the present invention, the proper positioning of graphic 21 can be accomplished in a simplified manner compared to previously known methods. Generally, the process for positioning the graphic according to the preferred embodiments of the present invention includes the steps of: (a) sensing a fixed phase position of the cutting means 39, setting a position flag corresponding to the fixed phase position of the cutting means 39, and determining a position encoder count when the position flag is set; (b) sensing the reference marker(s) 21a associated with the graphic 21, setting a reference marker flag corresponding to the position of graphic 21 associated with the sensed reference marker(s) 21a, and determining a reference marker encoder count when the reference marker flag is set; (c) determining the relative positional difference between the reference marker encoder count and the position encoder count; (d) comparing the determined relative positional difference to a predetermined set-point value; and (e) adjusting the position of the graphic 21 associated with the sensed reference marker(s) 21a to compensate for any variance between the determined relative positional difference and the predetermined set-point value.

In the preferred embodiment shown in FIG. 4A, the position of graphic 21 is adjusted using servodrive 38. Servodrive 38 adjusts the position of graphic 21 by controlling the speed at which the master roll 32 is conveyed. Feed-forward control is employed. The speed at which master roll 32 is conveyed is based on a comparison of the determined relative positional difference of the cutting means 39 with respect to a predetermined set-point value, as described in more detail below. The predetermined set-point value can be related to various manufacturing line parameters, such as the distance between sensor 35 and cutting means 39. It is a particular advantage of the present invention that the preferred registration process only relies on this simple feed-forward control, without the need for complex feed-back control systems.

More particularly, the position of the cutting means 39 can be sensed using a proximity switch (not shown). Based on this switch, the cutting means position flag is set to indicate where the cutting means is located along a predetermined position continuum. The predetermined position can be the cut position, or any other fixed position of the cutting means. The proximity switch can detect the falling edge of the flag, and the encoder count is noted at the time when the proximity switch detects the falling edge of the flag. Preferably, the encoder count ranges from 0 to 1. If necessary, the signal from the flag or the proximity switch can be filtered to obtain a more constant signal.

As discussed above, the reference marker 21a can be sensed using a photo-eye or optical detector 35. Preferably, the photo-eye 35 senses the reference marker flag at the falling edge of the reference marker 21a, and an encoder count is stored at the time when the photo-eye senses the flag. The encoder count preferably ranges from 0 to 1.

The base difference between the position encoder count and the reference marker encoder count can then be determined through simple subtraction. If the difference is negative, a normalizing constant of 1 can be added to the difference to thereby result in a positive value. In a particularly preferred embodiment, the relative positional difference between the reference marker encoder count and the position encoder count can then be determined by converting the base encoder count difference into units corresponding to the length of master roll 32 associated with the encoder count difference. Generally, this can be accomplished by multiplying the base encoder count difference by the rate at which the master roll 32 is being supplied.

This measured, relative positional difference between the reference marker encoder count and the position encoder count can then be compared to a predetermined set point value. Preferably, the predetermined set point value corresponds to the proper difference between the encoder counts when the reference marker 21a and the cutting means 29 are in proper synchronization.

Once the deviation between the measured, relative positional difference and the set point relative positional difference is determined, the position of the graphic 21 corresponding to the sensed reference marker 21a can be adjusted by adjusting servodrive 38 to compensate for the deviation. Generally, if the deviation is positive, the reference marker (and therefore the graphic) is too far away from the cutting means and the compensation will be done in the positive direction (the machine direction). On the other hand, if the deviation is negative, the reference marker (and thus the graphic) is too close to the cutting means and the compensation will be done in the negative direction. The compensation can preferably be accomplished by adjusting the servodrive 38. Further, if desired, the servodrive 38 can respond to each sensed reference marker 21a. Alternatively, the deviations from a number of sensed reference markers 21a can be averaged, and the servodrive 38 can respond to the average deviation.

In sum, the above method for properly placing graphics on a moving web allows for the automated manufacture of absorbent articles including at least one graphic thereon, wherein the reference marker used to sense the location of the graphic in the manufacturing line is not incorporated into the final product.

Another advantage of the present invention is that it allows for simplified automated manufacture of a "variety pack" of absorbent articles. The term "variety pack" refers to a set of individual absorbent articles continuously manufactured in-line, wherein each absorbent article includes at least one graphic thereon, and wherein at least one graphic included on each individual absorbent article differs from at least one graphic on adjacent absorbent articles in the manufacturing line. In the production of a variety pack of absorbent articles, the graphics can be provided from a master roll 32 as depicted in FIGS. 5A–5E.

FIGS. 5A–5E show various preferred configurations for the master roll 32. FIG. 5A shows a configuration wherein the reference markers 21a are positioned above the operatively associated graphics 21. Separation lines 21b indicate preferred divisions between the graphics. Graphics G1–G4 represent four distinct graphics, each of which differ from the others. With such a configuration, every fourth absorbent article will have the same graphics. As such, the "set" of absorbent articles in the variety pack will include four repeating articles. However, it should be understood that such a configuration with four absorbent articles in a set is merely an exemplification and the invention is not so limited. The set can include any desired number of absorbent articles, each containing a graphic. Likewise, the master roll 32 can include any desired number of distinct graphics.

FIG. 5C illustrates the removal of the reference markers 21a from the remainder of the master roll 32. FIGS. 5B and 5D show similar configurations wherein the reference markers 21a are located adjacent the operatively associated graphics 21. Finally, FIG. 5E demonstrates a preferred embodiment wherein the master roll comprises two aesthetically corresponding graphics 21 and 21', as described above.

The invention has been described in connection with the above preferred embodiments. These embodiments, however, are merely illustrative and the invention is not restricted thereto. It will be understood by those skilled in the art that other variations and modifications can easily be made within the scope of the invention as defined by the appended claims.

What is claimed is:

1. A method of making a variety pack of disposable absorbent articles in which a plurality of absorbent articles are contained within the variety pack, each absorbent article within the variety pack includes a graphic positioned on the absorbent article in at least the front or rear waist region of the absorbent article and each variety pack of absorbent articles contains a plurality of absorbent articles wherein at least two absorbent articles in the variety pack have graphics different from one another, the method comprising:

(a) providing a first continuously moving graphic layer, a second continuously moving nonwoven outer covering layer, and a cutting means; wherein the first continuously moving graphic layer includes a plurality of predetermined, discrete graphics and a plurality of reference markers printed thereon, wherein at least one reference marker is operatively associated with each of said plurality of predetermined, discrete graphics;

(b) sensing the location of at least one of said plurality of predetermined, discrete graphics using the at least one reference marker that is operatively associated with the at least one of said plurality of predetermined, discrete graphics;

(c) joining the graphics with the second continuously moving nonwoven outer covering layer;

(d) cutting said first continuously moving graphic layer into individual segments at a predetermined position between each of said plurality of predetermined, discrete graphics with said cutting means; wherein each of said individual segments cut from the first continuously moving graphic layer include thereon one of said plurality of predetermined, discrete graphics;

(e) packaging the absorbent articles produced in steps (a)–(e) to form the variety pack; and (f) removing the at least one reference marker in used in step (b).

2. The method of claim 1 wherein the graphic comprises a patch.

3. The method of claim 1 wherein the patch is positioned on at least the front waist portion of the absorbent article.

4. The method of claim 1 further comprising the step of providing different graphics on adjacent absorbent articles in the variety pack.

5. The method of claim 1 wherein the second continuously moving nonwoven layer forms an outer cover to the absorbent article.

6. The method of claim 1, wherein the packaging step comprises conveying the absorbent articles to a tack hold.

* * * * *